(12) United States Patent
Kasuga et al.

(10) Patent No.: US 8,076,509 B2
(45) Date of Patent: Dec. 13, 2011

(54) PROCESS FOR PRODUCING ACRYLIC ACID

(75) Inventors: Hiroto Kasuga, Himeji (JP); Etsushige Matsunami, Himeji (JP); Masafumi Sugio, Kobe (JP)

(73) Assignee: Nippon Shokubai Co., Ltd., Osaka (JP)

( * ) Notice: Subject to any disclaimer, the term of this patent is extended or adjusted under 35 U.S.C. 154(b) by 291 days.

(21) Appl. No.: 12/312,801

(22) PCT Filed: Nov. 28, 2007

(86) PCT No.: PCT/JP2007/072966
§ 371 (c)(1),
(2), (4) Date: May 26, 2009

(87) PCT Pub. No.: WO2008/066079
PCT Pub. Date: Jun. 5, 2008

(65) Prior Publication Data
US 2010/0010260 A1    Jan. 14, 2010

(30) Foreign Application Priority Data
Dec. 1, 2006   (JP) .................. 2006-325946

(51) Int. Cl.
*C07C 51/16*   (2006.01)
(52) U.S. Cl. ........................................... 562/532
(58) Field of Classification Search ........... 562/532
See application file for complete search history.

(56) References Cited

U.S. PATENT DOCUMENTS

| | | | |
|---|---|---|---|
| 4,093,776 A | 6/1978 | Aoki et al. | |
| 4,286,082 A | 8/1981 | Tsubakimoto et al. | |
| 4,367,323 A | 1/1983 | Kitamura et al. | |
| 4,446,261 A | 5/1984 | Yamasaki et al. | |
| 4,625,001 A | 11/1986 | Tsubakimoto et al. | |
| 4,683,274 A | 7/1987 | Nakamura et al. | |
| 4,873,299 A | 10/1989 | Nowakowsky et al. | |
| 4,973,632 A | 11/1990 | Nagasuna et al. | |
| 4,985,518 A | 1/1991 | Alexander et al. | |
| 5,124,416 A | 6/1992 | Haruna et al. | |
| 5,145,906 A | 9/1992 | Chambers et al. | |
| 5,164,459 A | 11/1992 | Kimura et al. | |
| 5,244,735 A | 9/1993 | Kimura et al. | |
| 5,250,640 A | 10/1993 | Irie et al. | |
| 5,264,495 A | 11/1993 | Irie et al. | |
| 5,380,808 A | 1/1995 | Sumiya et al. | |
| 6,174,978 B1 | 1/2001 | Hatsuda et al. | |
| 6,194,531 B1 | 2/2001 | Hatsuda et al. | |
| 6,458,740 B2 | 10/2002 | Kasuga et al. | |
| 7,910,771 B2 * | 3/2011 | Dubois et al. | 562/532 |
| 2001/0029233 A1 | 10/2001 | Kasuga et al. | |
| 2007/0129570 A1 | 6/2007 | Shima et al. | |
| 2008/0131945 A1 | 6/2008 | Toraya et al. | |
| 2008/0183013 A1 | 7/2008 | Dubois et al. | |
| 2008/0214880 A1 | 9/2008 | Dubois et al. | |

FOREIGN PATENT DOCUMENTS

| | | |
|---|---|---|
| EP | 0811636 A1 | 12/1997 |
| EP | 0922717 A1 | 6/1999 |
| EP | 0955086 A2 | 11/1999 |
| JP | 3-218334 A | 9/1991 |
| JP | 8-206504 A | 8/1996 |
| JP | 2001-246260 A | 9/2001 |
| JP | 2005-102533 A | 4/2005 |
| JP | 2005-213225 A | 8/2005 |
| WO | WO 2006/087084 A2 | 8/2006 |
| WO | WO 2006/114506 A1 | 11/2006 |
| WO | WO 2008/007002 A2 | 1/2008 |

* cited by examiner

Primary Examiner — Taylor Victor Oh

(57) ABSTRACT

The present invention provides a process for producing acrylic acid from glycerin with a catalyst having a prolonged life. In the process for producing acrylic acid from glycerin, a molar ratio of oxygen to glycerin in a raw material gas is set to be not lower than 0.8 and not higher than 20.

2 Claims, No Drawings

PROCESS FOR PRODUCING ACRYLIC ACID

This is the U.S. national phase of International Application No. PCT/JP2007/072966, filed Nov. 28, 2007, which claims priority from Japanese Patent Application No. 2006-325946 filed Dec. 1, 2006.

TECHNICAL FIELD

The present invention relates to a process for producing acrylic acid from glycerin by one step reaction.

BACKGROUND ART

Biodiesels produced from vegetable oils have drawn much attention as alternate fuels for fossil fuels and also in terms of a small discharge amount of carbon dioxide, and therefore, an increase in demand for biodiesels has been expected. Since the production of such biodiesels is accompanied by the formation of glycerin as a by-product, it is required to make effective use of glycerin. An embodiment of making use of glycerin is to use glycerin as a raw material for acrolein, and acrolein is further used as a raw material of acrylic acid.

Japanese Patent Laid-open Publication (Kokai) No. 2005-213225 discloses two processes for producing acrylic acid by oxidation of glycerin. The first process disclosed in this publication is a process for producing acrylic acid by producing a gaseous substance with gas-phase dehydration of glycerin and carrying out oxidation of the gaseous substance. That is, this first process is a two-step reaction process comprising dehydration of glycerin and oxidation of acrolein, both of which occur in different reaction systems. The second process is a process for producing acrylic acid from glycerin using a mixed catalyst composed of a catalyst for dehydration and a catalyst for gas-phase oxidation or using a catalyst having both the function of a catalyst for dehydration and the function of a catalyst for gas-phase oxidation. That is, the second process is a one-step reaction process comprising dehydration of glycerin and oxidation of acrolein, both of which occur in the same reaction system. As specific examples of the catalysts to be used in the above first process, there are disclosed catalysts for dehydration carrying phosphoric acid supported on an α-alumina carrier; and catalysts for oxidation which are Mo—V—W—Cu type composite oxides. Further, as specific examples of the catalyst to be used in the above second process, there are disclosed mixed catalysts composed of catalysts for dehydration carrying phosphoric acid supported on an α-alumina carrier and catalysts for oxidation which are Mo—V—W—Cu type composite oxides; and catalysts carrying Mo—V—W—Cu type composite oxides supported on α-alumina carrying phosphoric acid (i.e., catalysts having both the function of catalysts for dehydration and the function of catalysts for oxidation).

First, the present inventors have proceeded with studies on the above two-step reaction process, and as a result, they have found that when acrylic acid is produced from glycerin under the reaction conditions described in the Japanese Patent Laid-open Publication (Kokai) No. 2005-213225, the performance of a catalyst for oxidation is drastically deteriorated. Further, they have also found that one factor for the deterioration of catalyst performance is phenol and hydroxyacetone, both of which are formed as by-products in the dehydration of glycerin.

When acrylic acid is produced by a two-step reaction process, it is desired to decrease the amounts of by-products such as phenol and hydroxyacetone for the purpose of suppressing the deterioration of catalyst performance for oxidation.

When acrylic acid is produced by a two-step reaction process, it needs a refining step for removing by-products by distillation or any other means from acrolein containing the by-products formed by the dehydration of glycerin in the first step for the purpose of giving a prolonged life of a catalyst for oxidation. However, there are concerns such as loss of acrolein during the refining step; and clogging of pipes, distillation towers, or others with polymers formed during the refining step because of high polymerizability of acrolein. Further, the number of steps for producing acrylic acid from glycerin is desired to be small for the purpose of producing acrylic acid at a lower cost.

By the way, International Publication WO 2006/087084 discloses a process for producing acrolein from glycerin as reaction of the first step in the two-step reaction process. Along with this disclosure, this publication also discloses that phenol, hydroxyacetone, and others are formed as by-products in the production of acrolein and that the amounts of these by-products are decreased if oxygen at an amount lower than the flammability range is allowed to coexist in the dehydration system of glycerin. When oxygen is allowed to coexist in the dehydration system of glycerin, the above by-products can be reduced; however, the reduction of the by-products cannot be said to be sufficient for using the resultant acrolein in the production of acrylic acid without refining.

Then, the present inventors have studied on the one-step reaction process disclosed in the Japanese Patent Laid-open Publication (Kokai) No. 2005-213225. That is, the present inventors have studied on the reaction of directly obtaining acrylic acid from glycerin using a catalyst containing a combination of phosphoric acid and a Mo—V—W—Cu type composite oxide. However, the activity of the catalyst is remarkably lowered and is therefore insufficient from an industrial point of view under the reaction conditions disclosed in the Japanese Patent Laid-open Publication (Kokai) No. 2005-213225.

DISCLOSURE OF THE INVENTION

In view of the above circumstances, it is an object of the invention to provide a process for producing acrylic acid using glycerin as a raw material with a catalyst having a prolonged life.

The present inventors have made further studies on the one-step reaction process, and as a result, they have found that if acrylic acid is produced from glycerin with a solid catalyst using a raw material gas containing oxygen at a specific amount or higher relative to glycerin, the catalyst is less deteriorated. They have further found that if a solid catalyst essentially containing molybdenum is used, the catalyst is particularly less deteriorated.

As means for achieving the above object, the present inventors have completed processes for producing acrylic acid according to the following (1) to (3):

(1) A process for producing acrylic acid from glycerin using a reactor provided with a solid catalyst, wherein a raw material gas to be introduced into an inside of the reactor contains glycerin and oxygen at a molar ratio of oxygen to glycerin in a range of not lower than 0.8 and not higher than 20.

(2) The process for producing acrylic acid according to the above (1), wherein a catalyst containing molybdenum as an essential component is used as the solid catalyst.

(3) The process for producing acrylic acid according to the above (1), wherein a catalyst containing molybdenum and vanadium as essential components is used as the solid catalyst.

According to the present invention, a raw material gas at a molar ratio of oxygen to glycerin in a range of not lower than 0.8 and not higher than 20 is used, and therefore, acrylic acid can be produced from glycerin without being accompanied by the drastic deterioration of a catalyst. As a result, it can be expected that acrylic acid can be produced at a low cost.

BEST MODE FOR CARRYING OUT THE INVENTION

The process for producing acrylic acid in this embodiment is a process for producing acrylic acid by gas-phase reaction in which a raw material gas containing at least glycerin and oxygen is introduced into an inside of a reactor arbitrarily selected from fixed bed reactors, moving bed reactors, fluidized bed reactors, and other reactors, and the raw material gas is brought into contact with a catalyst.

A glycerin source of the above raw material gas may be any of refined products of glycerin, crude products of glycerin, and aqueous glycerin solutions. On the other hand, pure oxygen, air, oxygen-enriched air, or others may be selected as an oxygen source, and the use of oxygen in air may be preferred from an economical point of view.

To adjust the constituent concentrations of a raw material gas, it may preferably contain a gas inert to the reaction in this embodiment. Examples of the inert gas may include water vapor, nitrogen gas, and carbon dioxide. An economically preferable inert gas is a gas after collecting acrylic acid from a gas obtained in the process for producing acrylic acid according to this embodiment (hereinafter, the gas may be referred to sometimes as the "gas after collection") or a gas after combusting organic substances remaining in the gas (hereinafter, the gas may be referred to sometimes as the "gas after combustion").

Water vapor is known to have an effect of narrowing the flammability range usually determined in accordance with organic substances and oxygen, and therefore, water vapor may be preferred to be contained as an inert gas in the raw material gas. Water vapor in the raw material gas may include water vapor added separately, water contained in the raw material glycerin, water in air when air is used as an oxygen source, water in the gas after collection when the gas is used as an inert gas, and water in the gas after combustion when the gas is used as an inert gas.

The concentration of glycerin in the raw material gas is from 0.1 to 20 mol %, preferably from 1 to 15 mol %, and more preferably from 2 to 12 mol %.

The molar ratio of oxygen to glycerin in the raw material gas is not lower than 0.8 and not higher than 20, preferably not lower than 1.0 and not higher than 15, and more preferably not lower than 1.0 and not higher than 10. The upper limit and lower limit of the oxygen concentration are not particularly limited so long as they meet the above molar ratio conditions. However, since air is economical to be used as an oxygen source, the oxygen concentration may appropriately be 20 mol % or lower, preferably 18 mol % or lower, and more preferably 15 mol % or lower.

When water vapor or a water vapor-containing gas is used as an inert gas, the concentration of water vapor is not particularly limited. However, if the concentration of water vapor is too high, it is not economical because there is required evaporation heat of water to be added to the raw material gas or a great amount of energy for cooling to obtain acrylic acid from the produced gas obtained by the process of this embodiment. Therefore, the concentration of water vapor may usually be 30 mol % or lower, preferably 25 mol % or lower, and more preferably 20 mol % or lower. The inert gas remaining in the raw material gas is composed of nitrogen, carbon dioxide, and others.

The flow rate of the raw material gas may be from 100 to 10,000 $hr^{-1}$ in terms of raw material gas flow rate (GHSV) per unit catalyst volume. It may preferably be from 500 to 5,000 $hr^{-1}$ and more preferably from 1,000 to 3,000 $hr^{-1}$ for the purpose of carrying out the production of acrylic acid with high efficiency from an economical point of view.

The reaction temperature may be from 200° C. to 400° C., preferably from 200° C. to 350° C., and more preferably 200° C. to 300° C.

The reaction pressure is not particularly limited, if it is within a range that glycerin is not condensed. The reaction pressure may usually be from 0.001 to 1 MPa and preferably from 0.01 to 0.5 MPa.

A solid catalyst is used as a catalyst of this embodiment. Preferred catalysts are those which contain molybdenum as an essential component. More preferred catalysts are those which contain a single oxide or composite oxide of molybdenum, or those which carry these oxides supported on a carrier. Still more preferred catalysts are molybdenum-vanadium type catalysts containing molybdenum and vanadium as essential components, and hetero-polyacid type catalysts containing phosphorus and molybdenum as essential components.

If any of the heretofore known methods for producing catalysts is employed, there can be prepared a catalyst to be used for the process for producing acrylic acid according to this embodiment. For example, molybdenum-vanadium type catalysts containing molybdenum and vanadium as essential components can be prepared by the method for producing a catalyst as described in Example 1 of Japanese Patent Laid-open Publication (Kokai) No. Hei 3-218334, comprising crushing and forming a solid material obtained by evaporating, to dryness, a solution containing ammonium paramolybdate, ammonium metavanadate, cupric nitrate, ammonium paratungstate, and zirconium oxide, and then drying and baking the formed material; or by the method for producing a catalyst as described in Example 1 of Japanese Patent Laid-open Publication (Kokai) No. Hei 8-206504, comprising depositing a solution containing ammonium paramolybdate, ammonium metavanadate, vanadium trioxide, cupric nitrate, cuprous oxide, and antimony trioxide to a carrier made of α-alumina, and then baking the carrier. Further, a hetero-polyacid type catalyst containing phosphorus and molybdenum as essential components can be prepared by the method for producing a catalyst as described in Example 1 of Japanese Patent Laid-open Publication (Kokai) No. 2001-246260, comprising forming a clay-like material obtained by heating for concentration of a mixed aqueous solution containing ammonium paramolybdate, molybdenum trioxide, ammonium metavanadate, pyridine, phosphoric acid, nitric acid, cupric nitrate, and cesium nitrate, and then drying and baking the formed material.

The shape of a catalyst, although it is not particularly limited, may be a spherical, column-like, ring-like, or saddle-like shape, and the size of a catalyst may usually be about 0.1 to 10 mm in terms of diameter.

According to the above process, acrylic acid can be produced. Acrylic acid produced using any of the already heretofore known techniques can be used as a raw material for producing acrylic acid derivatives such as 1,3-propanediol, polyacrylic acid, and polyacrylate. Accordingly, it is, of course, possible to incorporate the above process for producing acrylic acid into a process for producing an acrylic acid derivative.

Then, when polyacrylic acid is produced using the obtained acrylic acid, polyacrylic acid which can be used as a water-absorbing resin can be produced using an aqueous solution polymerization method or a reversed phase suspension polymerization method. In this regard, the aqueous solution polymerization method is a method for polymerizing acrylic acid in an aqueous acrylic acid solution without using a dispersion solvent, and is disclosed in, for example, U.S. Pat. Nos. 4,625,001, 4,873,299, 4,286,082, 4,973,632, 4,985,518, 5,124,416, 5,250,640, 5,264,495, 5,145,906, and 5,380,808, as well as European Patents Nos. 0 811 636, 0 955 086, and 0 922 717. Further, the reversed phase suspension polymerization method is a polymerization method comprising suspending an aqueous solution of acrylic acid as a monomer in a hydrophobic organic solvent, and is disclosed in U.S. Pat. Nos. 4,093,776, 4,367,323, 4,446,261, 4,683,274, and 5,244,735.

EXAMPLES

The present invention will be described below in more detail by way of Examples, but the scope of the invention is not limited only to these Examples. In the following, unless otherwise indicated, "%" indicates "% by mass" and "part(s)" indicates "part(s) by mass."

Catalyst Preparation Example 1

According to the method as described in Example 1 of the Japanese Patent Laid-open Publication (Kokai) No. Hei 3-218334, zirconium oxide obtained by baking zirconyl nitrate at 750° C. for 3 hours and then crushing the resultant material by jet stream was added to a solution obtained by mixing an aqueous solution of ammonium paramolybdate and ammonium metavanadate with an aqueous solution of cupric nitrate and ammonium paratungstate. This mixture was heated for concentration to dryness and then dried. The resultant dried mixture was crushed, followed by forming and heat treatment at 400° C. for 6 hours, to obtain a catalyst 1 having a composition ratio of metal elements excluding oxygen as $Mo_{12}V_4W_{2.5}Cu_2Zr_2$.

Catalyst Preparation Example 2

According to the method as described in Example 1 of the Japanese Patent Laid-open Publication (Kokai) No. 2001-246260, a mixed solution containing ammonium paramolybdate, molybdenum trioxide, ammonium metavanadate, pyridine, phosphoric acid, nitric acid, cesium nitrate, and cupric nitrate was prepared and heated for concentration. The resultant clay-like material was formed, followed by drying and baking, to obtain a catalyst 2 having a composition ratio of metal elements excluding oxygen as $P_{1.3}Mo_{12}V_1Cu_{0.1}Cs_{1.2}$.

Example 1

A fixed bed reactor was prepared by filling a stainless steel reaction tube (having an inner diameter of 10 mm and a length of 500 mm) with the catalyst 1 which was coarsely crushed and classified into sizes of from 0.7 to 2.0 mm. This reactor was immersed in a salt bath at 250° C. Then, a raw material gas was allowed to pass though the reactor at a flow rate of 2,000 hr$^{-1}$. The raw material gas used at that time was a gas composed of an evaporated gas of a 60 wt % aqueous glycerin solution, nitrogen, and air. The composition of the raw material gas was 2.8 mol % glycerin, 10.0 mol % oxygen, 9.6 mol % water, and 77.6 mol % nitrogen. The molar ratio of oxygen to glycerin was 3.6. The gas flowing out of the reactor was liquefied by cooling and collected for 30 minutes extending from 0.5 to 1 hours and for 30 minutes extending from 23.5 to 24.0 hours after allowing the raw material gas to pass though the reactor (hereinafter, the material liquefied by cooling the collected flowing-out gas is referred to as the "flowing-out material").

Then, the qualitative and quantitative analyses of the flowing-out material were carried out by gas chromatography (GC). As a result of the qualitative analysis by GC, acrolein was detected together with glycerin and acrylic acid. Further, as a result of the quantitative analysis, conversion rate, yield of acrylic acid, and yield of acrolein were calculated. In this regard, the conversion rate is a value calculated by the following formula (1) and the yield of acrylic acid is a value calculated by the following formula (2).

[Formula 1]

$$\text{Conversion rate (\%)} = (1 - \text{number of moles for glycerin in collected flowing-out material}/\text{number of moles for glycerin allowed to pass though reactor for 30 minutes}) \times 100 \qquad \text{Formula (1)}$$

[Formula 2]

$$\text{Yield of acrylic acid} = (\text{number of moles for acrylic acid}/\text{number of moles for glycerin allowed to pass through reactor for 30 minutes}) \times 100 \qquad \text{Formula (2)}$$

The conversion rate of glycerin for a period extending from 0.5 to 1 hour was 100 mol %, the yield of acrylic acid was 16.5 mol %, and the yield of acrolein was 0.8 mol %. Further, the conversion rate for a period extending from 23.5 to 24 hours was 100 mol %, the yield of acrylic acid was 17.1 mol %, and the yield of acrolein was 0.5 mol %.

Example 2

Acrylic acid was produced in the same manner as described in Example 1, except that the composition of a raw material gas was set to be 2.8 mol % glycerin, 4.2 mol % oxygen, 9.6 mol % water, and 83.6 mol % nitrogen, and the molar ratio of oxygen to glycerin was set to be 1.5. The conversion rate of glycerin for a period extending from 0.5 to 1 hour was 100 mol %, the yield of acrylic acid was 26.0 mol %, and the yield of acrolein was 0.9 mol %. Further, the conversion rate for a period extending from 23.5 to 24 hours was 100 mol %, the yield of acrylic acid was 27.2 mol %, and the yield of acrolein was 1.2 mol %.

Example 3

Acrylic acid was produced in the same manner as described in Example 1, except that the catalyst 2 was used in place of the catalyst 1. The conversion rate of glycerin for a period extending from 0.5 to 1 hour was 100 mol %, the yield of acrylic acid was 8.1 mol %, and the yield of acrolein was 25.5 mol %. Further, the conversion rate for a period extending from 23.5 to 24 hours was 100 mol %, the yield of acrylic acid was 7.2 mol %, and the yield of acrolein was 26.2 mol %.

Example 4

Acrylic acid was produced in the same manner as described in Example 1, except that the composition of a raw material gas was set to be 7.8 mol % glycerin, 12.0 mol % oxygen, 10.0 mol % water, 70.2 mol % nitrogen, the molar ratio of oxygen to glycerin was set to be 1.54, and the reaction temperature was set to be 230° C. The conversion rate of glycerin for a period extending from 0.5 to 1 hour was 100 mol %, the yield of acrylic acid was 25.1 mol %, and the yield of acrolein was 0.8 mol %. Further, the conversion rate for a period extending from 23.5 to 24 hours was 100 mol %, the yield of acrylic acid was 25.9 mol %, and the yield of acrolein was 0.7 mol %.

Example 5

Acrylic acid was produced in the same manner as described in Example 4, except that the composition of a raw material gas was set to be 6.0 mol % glycerin, 12.0 mol % oxygen, 7.7 mol % water, and 74.3 mol % nitrogen, and the molar ratio of oxygen to glycerin was set to be 2.0. The conversion rate of glycerin for a period extending from 0.5 to 1 hour was 100 mol %, the yield of acrylic acid was 28.0 mol %, and the yield of acrolein was 0.8 mol %. Further, the conversion rate for a period extending from 23.5 to 24 hours was 100 mol %, the yield of acrylic acid was 27.9 mol %, and the yield of acrolein was 0.7 mol %.

Example 6

Acrylic acid was produced in the same manner as described in Example 1, except that the catalyst 2 was used in place of the catalyst 1, the composition of a raw material gas was set to be 2.0 mol % glycerin, 15.0 mol % oxygen, 4.5 mol % water, and 78.5 mol % nitrogen, the molar ratio of oxygen to glycerin was set to be 7.5, and the reaction temperature was set to be 230° C. The conversion rate of glycerin for a period extending from 0.5 to 1 hour was 100 mol %, the yield of acrylic acid was 12.8 mol %, and the yield of acrolein was 20.5 mol %. Further, the conversion rate for a period extending from 23.5 to 24 hours was 100 mol %, the yield of acrylic acid was 12.7 mol %, and the yield of acrolein was 20.2 mol %.

Example 7

Acrylic acid was produced in the same manner as described in Example 1, except that the catalyst 2 was used in place of the catalyst 1, the composition of a raw material gas was set to be 6.0 mol % glycerin, 12.0 mol % oxygen, 7.7 mol % water, and 74.3 mol % nitrogen, the molar ratio of oxygen to glycerin was set to be 2.0, and the reaction temperature was set to be 230° C. The conversion rate of glycerin for a period extending from 0.5 to 1 hour was 100 mol %, the yield of acrylic acid was 16.7 mol %, and the yield of acrolein was 14.7 mol %. Further, the conversion rate for a period extending from 23.5 to 24 hours was 100 mol %, the yield of acrylic acid was 16.8 mol %, and the yield of acrolein was 14.8 mol %.

Comparative Example 1

Acrylic acid was produced in the same manner as described in Example 1, except that the composition of a raw material gas was set to be 2.8 mol % glycerin, 1.7 mol % oxygen, 9.6 mol % water, and 86.0 mol % nitrogen, and the molar ratio of oxygen to glycerin was set to be 0.6. The conversion rate of glycerin for a period extending from 0.5 to 1 hour was 100 mol %, the yield of acrylic acid was 46.7 mol %, and the yield of acrolein was 0.4 mol %. Further, the conversion rate for a period extending from 23.5 to 24 hours was 61.7 mol %, the yield of acrylic acid was 13.3 mol %, and the yield of acrolein was 8.1 mol %.

Comparative Example 2

A zeolite (catalyst 3) known as a catalyst for dehydration of glycerin was used. The catalyst 3 had a ratio of Si to Al of 100. Acrylic acid was produced in the same manner as described in Example 1, except that the composition of a raw material gas was set to be 26.7 mol % of glycerin, 8.3 mol % oxygen, 34.0 mol % water, and 31.0 mol % nitrogen, the molar ratio of oxygen to glycerin was set to be 0.31, and the reaction temperature was set to be 360° C. The conversion rate of glycerin for a period extending from 0.5 to 1 hour was 100 mol %, no acrylic acid was detected, and the yield of acrolein was 58.9 mol %. Further, the conversion rate for a period extending from 23.5 to 24 hours was 91.3 mol %, no acrylic acid was detected, and the yield of acrolein was 4.3.0 mol %.

With respect to the conversion rate of glycerin and the yield of acrylic acid, the ratios of their values for a period extending from 23.5 to 24 hours to their values for a period extending from 0.5 to 1 hour are shown as the changes of conversion rate and the changes of yield, respectively, in Table 1. The change of conversion rate and the change of yield both show a small change over time of catalyst performance when their values are closer to 1; an improvement in catalyst performance when their values are 1 or higher; and a drastic deterioration in catalyst performance when their values are lower than 1.

TABLE 1

| | Catalyst | Glycerin Concentration (mol %) | Oxygen Concentration (mol %) | Oxygen/glycerin (molar ratio) | Change of conversion rate | Change of yield |
|---|---|---|---|---|---|---|
| Example 1 | Catalyst 1 | 2.8 | 10.0 | 3.6 | 1.00 | 1.04 |
| Example 2 | Catalyst 1 | 2.8 | 4.2 | 1.5 | 1.00 | 1.05 |
| Example 3 | Catalyst 2 | 2.8 | 10.0 | 3.6 | 1.00 | 0.89 |
| Example 4 | Catalyst 1 | 7.8 | 12.0 | 1.54 | 1.00 | 1.03 |
| Example 5 | Catalyst 1 | 6.0 | 12.0 | 2.0 | 1.00 | 1.00 |
| Example 6 | Catalyst 2 | 2.0 | 15.0 | 7.5 | 1.00 | 0.99 |
| Example 7 | Catalyst 2 | 6.0 | 12.0 | 2.0 | 1.00 | 1.01 |
| Comparative Example 1 | Catalyst 1 | 2.8 | 1.7 | 0.6 | 0.62 | 0.28 |
| Comparative Example 2 | Catalyst 3 | 26.7 | 8.3 | 0.31 | 0.91 | — |

Change of conversion rate = (Conversion rate for a period extending from 23.5 to 24 hours)/(Conversion rate for a period extending from 0.5 to 1 hour)
Change of yield = (Yield for a period extending from 23.5 to 24 hours)/(Yield for a period extending from 0.5 to 1 hour)

As shown in Table 1, when the ratio of oxygen to glycerin was 0.6, the change of conversion rate was 0.62 and the change of yield was 0.28, and therefore, it is found that catalyst performance was remarkably lowered. On the other hand, when the ratio of oxygen to glycerin was 0.8 or higher, the change of conversion rate was 1.0 and the change of yield was from 0.89 to 1.04, and therefore, it is found that catalyst performance was stable.

In the production of acrylic acid from glycerin, when the molar ratio of oxygen to glycerin in the raw material gas is not lower than 0.8 and not higher than 20, acrylic acid can be obtained from glycerin without being accompanied by the drastic deterioration of a catalyst.

A raw material gas was allowed to pass though the reactor in the same manner as described in Example 1, and the gas flowing out of the reactor was absorbed in water to obtain an aqueous acrylic acid solution. Using this aqueous acrylic acid solution as a raw material, a water-absorbing resin was produced. The process for producing the water-absorbing resin and the physical properties of the water-absorbing resin were as follows.

Production of Water-Absorbing Resin:

The aqueous acrylic acid solution was supplied to a solvent separation tower, and low boiling point impurities such as water and acetic acid were removed from the aqueous acrylic acid solution by azeotropic distillation. Then, the aqueous acrylic acid solution was supplied to the tower bottom of a high boiling point impurity separation tower having fifty weir-free porous plates and distilled while setting the reflux ratio to be 2. At the time of the distillation in this high boiling point impurity separation tower, p-methoxyphenol was charged from the top of the separation tower and hydrazine hydrate was charged on the 25-th weir-free porous plate from the bottom of the separation tower, to thereby obtain an acrylic acid-containing composition containing acrylic acid and 20 ppm by mass of p-methoxyphenol from the top of the separation tower.

Then, 72.07 g of the above acrylic acid-containing composition, 293.06 g of ion exchanged water, and polyethylene glycol diacrylate (the average addition mole number of ethylene oxide thereof was 8.2) in a concentration of 0.05 mol % relative to the total amount of monomers were mixed to prepare an aqueous monomer solution having an acrylic acid concentration of 20 mol %, a p-methoxyphenol concentration of 20 ppm by mass, and a neutralization rate of 0 mol %.

The total amount of the aqueous monomer solution at a temperature of 20° C., which had been prepared as described above, was charged in a vessel for polymerization (a cylindrical vessel made of polypropylene, having a capacity of 1 L), into which nitrogen gas was blown to allow the concentration of dissolved oxygen to be 1 ppm or lower in the aqueous monomer solution. Then, the vessel for polymerization was kept in an adiabatic state, to which an aqueous solution containing 0.12 g of sodium persulfate as a polymerization initiator and an aqueous solution containing 0.0018 g of L-ascorbic acid were added. Then, the polymerization of acrylic acid was promoted until it passed 30 minutes from the time when the temperature of the aqueous monomer solution became a peak temperature, to thereby obtain a water-containing gel polymer. The water-containing gel polymer was made minute to a size of about 1 mm, to which 62.5 g of a 48 wt % aqueous sodium hydroxide solution was added to neutralize 75 mol % of the acid groups of the water-containing gel polymer. After the neutralization, the calculated polymerization ratio of the water-containing gel polymer was 98.4%. Then, the water-containing gel polymer was spread over a net having a mesh of 850 μm and dried in hot blow of a gas (having a dew point of 60° C.) at 160° C. for 60 minutes, crushed by a vibration mill, and further classified with a JIS standard sieve having a mesh of 850 μm. The powder passing the sieve in this classification was obtained as a water-absorbing resin.

Physical Properties of Water-Absorbing Resin:

The physical properties of the water-absorbing resin were 50 times as the absorption factor to physiological saline, 48 times as the absorption factor to artificial urine, and 9% by mass of water-soluble components. In this regard, the measurement methods of the respective physical properties of the water-absorbing resin were as follows.

Absorption Factor to Physiological Saline:

According to the absorption factor calculation method under no load conditions as disclosed in U.S. Pat. No. 5,164,459, the absorption factor was calculated as follows. First, 0.2 g of the water-absorbing resin was charged in a tea bag type non-woven fabric bag (having a size of 40 mm×150 mm), and then, the opening portion of the non-woven fabric bag was closed and sealed. The non-woven fabric bag was immersed in 100 g of physiological saline (i.e., a 0.9 wt % aqueous sodium chloride solution) at a temperature of 25±3° C. for 30 minutes. After the immersion, draining was carried out. The absorption factor $((W1-W2)g/0.2\ g)$ of the water-absorbing resin to the physiological saline was calculated from the mass (W2) of the water-absorbing resin and non-woven fabric bag before immersion in the physiological saline and the mass (W1) of the water-absorbing resin and non-woven fabric bag after immersion and draining measured, respectively, in this series of operations.

Absorption Factor to Artificial Urine:

According to the absorption factor calculation method under no load conditions as disclosed in U.S. Pat. No. 5,164,459, the absorption factor was calculated as follows. First, 0.2 g of the water-absorbing resin was charged in a tea bag type non-woven fabric bag (having a size of 60 mm×60 mm), and then, the opening portion of the non-woven fabric bag was closed and sealed. The non-woven fabric bag was immersed in 100 g of artificial urine at a temperature of 25±3° C. for 60 minutes. After the immersion, draining was carried out at 250 G for 3 minutes by using a centrifuge machine. The absorption factor $((W3-W4)g/0.2\ g)$ of the water-absorbing resin to the artificial urine was calculated from the mass (W4) of the water-absorbing resin and non-woven fabric bag before immersion in the artificial urine and the mass (W3) of the water-absorbing resin and non-woven fabric bag after immersion and draining measured, respectively, in this series of operations. In this regard, the artificial urine used herein was artificial urine commercially available by Jayco Inc. (i.e., a solution obtained by dissolving 2.0 g of potassium chloride, 2.0 g of sodium sulfate, 0.85 g of ammonium dihydrogenphosphate, 0.15 g of ammonium monohydrogenphosphate, 0.19 g of calcium chloride, and 0.23 g of magnesium chloride in 1 L of distilled water).

Water-Soluble Components:

First, 500 mg of the water-absorbing resin was dispersed in 1,000 ml of deionized water at room temperature, and the mixture was stirred by a magnetic stirrer for 16 hours. Then, the water-absorbing resin in the form of a swollen gel was filtered with a paper filter (No. 6, available from Toyo Roshi Kaisha., Ltd.). Then, the water-absorbing resin in the filtrate was subjected to colloid titration to determine the water-soluble components in the water-absorbing resin.

INDUSTRIAL APPLICABILITY

According to the present invention, in the process for producing acrylic acid from glycerin where the molar ratio of oxygen to glycerin in a raw material gas is not lower than 0.8 and not higher than 20, acrylic acid can be obtained from glycerin without being accompanied by the drastic deterioration of a catalyst, and therefore, acrylic acid can be produced at a lower cost.

The invention claimed is:

1. A process for producing acrylic acid from glycerin using a reactor, wherein a raw material gas to be introduced into an inside of the reactor contains glycerin and oxygen at a molar ratio of oxygen to glycerin in a range of not lower than 0.8 and not higher than 20, a catalyst containing molybdenum as an essential component is used, and wherein raw material gas contains water vapor of not higher than 30 mol %.

2. The process for producing acrylic acid according to claim 1, wherein a catalyst containing molybdenum and vanadium as essential components is used.

* * * * *